US005981701A

United States Patent [19]

Wallach et al.

[11] Patent Number: 5,981,701
[45] Date of Patent: Nov. 9, 1999

[54] TUMOR NECROSIS FACTOR INHIBITORY PROTEIN AND ITS PURIFICATION

[75] Inventors: David Wallach, Rehovot, Israel; Hartmut Engelmann, Munich, Germany; Dan Aderka, Holon; Menachem Rubinstein, Givat Schmuel, both of Israel

[73] Assignee: Yeda Research and Development Company Limited, Rehovot, Israel

[21] Appl. No.: 08/474,691

[22] Filed: Jun. 7, 1995

Related U.S. Application Data

[62] Division of application No. 07/876,828, Apr. 30, 1992, Pat. No. 5,695,953, which is a continuation of application No. 07/243,092, Sep. 12, 1988, abandoned.

[30] Foreign Application Priority Data

Sep. 13, 1987 [IL] Israel ........................................ 83878

[51] Int. Cl.$^6$ ................................................. C07K 14/705
[52] U.S. Cl. ........................... 530/350; 530/351; 530/344; 530/395; 514/2; 514/8; 514/12; 424/85.1
[58] Field of Search .............................. 514/2, 21, 8, 12; 530/350, 344, 395, 351; 424/85.1, 85.11

[56] References Cited

U.S. PATENT DOCUMENTS

| | | | |
|---|---|---|---|
| 4,966,888 | 10/1990 | Saxena et al. ................................. | 514/2 |
| 5,136,021 | 8/1992 | Dembinski et al. ...................... | 530/350 |
| 5,344,915 | 9/1994 | LeMaire et al. . | |
| 5,359,037 | 10/1994 | Wallach et al. . | |
| 5,395,760 | 3/1995 | Smith et al. ............................ | 435/69.1 |
| 5,447,851 | 9/1995 | Beutler et al. . | |
| 5,478,925 | 12/1995 | Wallach et al. . | |
| 5,512,544 | 4/1996 | Wallach et al. . | |
| 5,605,690 | 2/1997 | Jacobs et al. . | |
| 5,610,279 | 3/1997 | Brockhaus et al. . | |
| 5,672,347 | 9/1997 | Aggarwal etal. . | |

FOREIGN PATENT DOCUMENTS

| | | |
|---|---|---|
| 0334165 | 9/1989 | European Pat. Off. . |
| 0433900 | 1/1991 | European Pat. Off. . |
| 2218101 | 11/1989 | United Kingdom . |

OTHER PUBLICATIONS

Seckinger et al. A Human Inhibitor of Tumor Necrosis Factor alpha. Journal of Experimental Medicine. pp. 1511–1516, Apr. 1988.

Loetsch, H. et al., "Purification and Partial Amino Acid Sequence Analysis of Two Distinct Tumor Necrosis Factor Receptors from HL60 Cells", *The Journal of Biological Chemistry*, vol. 265, No. 33, pp. 20131–20138, Nov. 25, 1990.

Peetre et al., "A Tumor Necrosis Factor Binding Protein is Present in Human Biological Fluids", *Eur. J. Haematol*, vol. 41, pp. 414–419, 1988.

Sechinger, et al., "A Human Inhibitor of Tumor Necrosis Factor α", *J. Exp. Med.*, vol. 167, pp. 1511–1516, Apr. 1988.

Lee, et al., "Generation of cDNA Probes Directed by Amino Acid Sequences", *Science*, vol. 239, pp. 1288–1291, 1988.

Hass, et al., "Characterization of Specific High Affinity Receptors for Human TNF . . . ", *J. of Biol. Chem.*, vol. 260, pp. 12214–12218, 1985.

Baglioni, et al., "Binding of TNF to High Affinity Receptors on HeLa and Lympheblastoid . . . ", *J. of Biol. Chem.*, vol. 260, pp. 13395–13397, 1985.

Israel, et al., "Binding of Human TNF–α to High Affinity Cell Surface Receptors . . . ", *Immunology Letters*, vol. 12, pp. 217–224, 1986.

Niitso, et al., "Receptor Protein for Physiologically Active Substances", *JPO Public Disclosure Bulletin*, vol. 61, p. 293924, Dec. 24, 1986.

Yoshie, et al., "Binding and Crosslinking of $^{125}$I–Labeled Recombinant Human TNF", *J. Biochem.*, vol. 100, pp. 531–541, 1986.

Suggs, et al., "Use of Synthetic Oligonucleotides as Hybridization Probes", *PNAS*, vol. 78, pp. 6613–6617, 1981.

Beutler, B. et al., "Passive Immunization Against Cachectin/Tumor Necrosis Factor Protects Mice from Lethal Effect of Endotoxin", *Science*, vol. 229, pp. 869–871, Aug. 30, 1985.

Creasy, A. A., et al., "A high molecular weight component of the human tumor necrosis factor receptor is associated with cytotoxicity", *PNAS*, vol. 84, pp. 3293–3297, May 1987.

Kasukabe, T. et al., "Purification of a Novel Growth Inhibitory Factor for Partially Differentiated Myeloid Leukemic Cells", *J. Biol. Chem.*, vol. 263, No. 11, pp. 5431–5435, Apr. 15, 1988.

Le, J., et al., "Biology of Disease: Tumor Necrosis Factor and Interleukin 1: Cytokines with Multiple Overlapping Biological Activities", *Lab. Investig.*, vol. 56, No. 3, pp. 234–248, 1987.

Liao, Z., et al., "Characterization of a Human Interleukin 1 Inhibitor", *J. Immunol.*, vol. 134, No. 6, pp. 3882–3886, Jun. 1985.

Seckinger, P., et al. "A Urine Inhibitor of Interleukin 1 Activity that Blocks Ligand Binding", *J. Immunol.*, vol. 139, No. 5, pp. 1546–1549, Sep. 1, 1987.

Tracey, J. et al., "Anti–cachectin/TNF monoclonal antibodies prevent septic shock during lethal bacteraemia", *Nature*, vol. 330, pp. 662–664, Dec. 17, 1987.

Tsujimoto, M., et al., "Characterization and Affinity Crosslinking of Receptors", *Archives of Biochem. and Biophysics*, vol. 249, No. 2, pp. 563–568, Sep. 1986.

Vitt, C. R., et al., "Biological and Structural Characterization of the Tumor Necrosis Factor Receptor on Multiple Cell Types: Relationship to Function", *Fed. Proc.*, vol. 46, p. 2117, 1987, abstract No. 1118.

(List continued on next page.)

*Primary Examiner*—Garnette D. Draper
*Attorney, Agent, or Firm*—Browdy and Neimark

[57] ABSTRACT

Tumor Necrosis Factor (TNF) Inhibitory Protein is isolated and substantially purified. It has the ability to inhibit: (a) the binding of TNF to its receptors, and (b) the cytotoxic effect of TNF. TNF Inhibitory Protein and salts, functional derivatives and active fractions thereof can be used to antagonize the deleterious effects of TNF.

3 Claims, 5 Drawing Sheets

OTHER PUBLICATIONS

Wallach, D., "Preparations of Lymphotoxin Induce Resistance to their Own Cytotoxic Effect", *J. Immunol.*, vol. 132, No. 5, pp. 2464–2469, May 1984.

Walsh, L. J., et al., "Isolation and Purification of ILS, an Interleukin 1 Inhibitor Produced by Human Gingival Epithelial Cells", *Clin. Exp. Immunol.*, vol. 68, pp. 366–374, 1987.

Ulsson et al, *Eur. J. Haematol* 42, 1989, pp. 270–278.
Engelmann et al *JBC* 264(20) 1989, pp. 11974–11980.
Seckinger et al *JBC* 264(20) 1989, pp. 11966–11973.
Engelmann et al, *JBC* 265(3) 1990, pp. 1531–1536.
Novick et al, *J Exp Med* 170, 1989, pp. 1409–1414.
Hahmann et al *JBC* 264(25) 1989, pp. 14927–14934.
Scheurich et al, *Int J Cancer* 38, 1986, pp. 127–133.
Kull et al, *PNAS* 82, 1985, pp. 5756–5760.

TUMOR NECROSIS FACTOR INHIBITORY PROTEIN AND ITS PURIFICATION

CROSS-REFERENCE TO RELATED APPLICATIONS

The present application is a divisional of U.S. application Ser. No. 07/876,828, filed Apr. 30, 1992 now U.S. Pat. No. 5,695,953 which is a continuation of U.S. application Ser. No. 07/243,092, filed Sep. 12, 1998, now abandoned.

FIELD OF THE INVENTION

This invention relates to substantially purified Tumor Necrosis Factor (TNF) Inhibitory Protein and salts, functional derivatives and active fractions thereof, having the ability to inhibit the binding of TNF to its receptors and the cytotoxic effect of TNF and which can be used against the deleterious effects of TNF. It also relates to a process for the purification of said TNF Inhibitory Protein, to its cloning and its production by recombinant DNA techniques. It further relates to pharmaceutical compositions comprising such a protein, or salts, functional derivatives and active fractions thereof, for protecting against the deleterious effects of TNF and to a method of medical treatment using the protein.

BACKGROUND OF THE INVENTION

Tumor Necrosis Factor-α (TNF-α) and Lymphotoxin or TNF-β (hereinafter, TNF refers to both TNF-α and TNF-β) are cytokines which have many effects on cells (Wallach, D. (1986) in: Interferon 7 (Ion Gresser, Ed.), pp. 83–122, Academic Press, London, and Beutler, B. and Cerami, A. (1987) New England J. Med. 316: 379–385). Both TNF-α and TNF-β initiate their effects by binding to specific cell surface receptors. Some of the effects are likely to be beneficial to the organism: they may destroy, for example, tumor cells or virus infected cells and augment antibacterial activities of granulocytes. But, quite clearly, both TNF-α and TNF-β have also effects which can be extensively deleterious. There is evidence that over production of TNF-α can play a major pathogenic role in several diseases. Thus effects of TNF-α, primarily on the vasculature, are now known to be a major cause for symptoms of septic shock (Tracey, K. J. et al. (1986) Science 234: 470–474). In some diseases, TNF may cause excessive loss of weight (cachexia) by suppressing activities of adipocytes and by causing anorexia and TNF-α was thus called cachectin. It was also described as a mediator of the damage to tissues in rheumatic disease (Beutler, op.cit.) and as a major mediator of the damage observed in graft-versus-host reactions.

There is therefore a necessity in finding out ways to eliminate or antagonize endogenously formed or exogenously administered TNF. Our first attempt in this direction was the development of monoclonal antibodies which neutralize the TNF-α cytotoxic activity and were shown to protect mice against the lethal effect of TNF-α under conditions mimicking elicitation of septic shock (as described in our U.S. patent application Ser. No. 06/808,262 of Dec. 12, 1985). However, therapy with murine monoclonal antibodies, especially if administered repetitively, may not always be advisable in humans. Therefore the need was felt for development of biological agents which could similarly antagonize the deleterious effects of TNF.

Prior to the filing date of the priority application of the present application, there was no information as to the existence of biological agents which could antagonize the cytotoxic activity of THF. There were publications describing uromodulin, a 85-kDa immunosuppressive glycoprotein isolated from the urine of pregnant women (Muchmore, Andrew V. and Decker, Jean M. (1985) Science 229:479–481), that was shown to be a high affinity ligand for and a potent inhibitor of interleukin 1 (IL-1) (Muchmore, Andrew V. and Decker, Jean M. (1986) J. Biol. Chem. 261:13404–13407; Brown, K. M. et al. (1986) Proc. Natl. Acad. Sci. U.S.A. 83:9119–9123). Uromodulin was later shown to be identical to the Tamm-Horsfall glycoprotein, the most abundant protein of renal origin in normal urine (Pennica, Diane et al. (1987) Science 236:83–88). Another inhibitor of IL-1 found in the urine of febrile patients was disclosed in some publications (Liao, Zenghua et al. (1984) J. Exp. Med. 159:126–136; Seckinger, Phillippe et al. (1987) J. Immunol. 139:1546–1549). It was shown that this urine inhibitor of IL-1 affects numerous biological activities of both forms of recombinant IL-1, IL-1α and IL-1β to the same extent. Although human TNF-α shares some of the biological activities of IL-1, this IL-1 inhibitor did not inhibit the biological activities of TNF-α (Seckinger, Phillippe et al. (1987) J. Immunol. 139:1541–1545).

Subsequent to the filing date of the priority application of the present application, it was disclosed that uromodulin and the Tamm-Horsfall glycoprotein bind recombinant IL-1α, IL-1β and TNF-α in a lectin-like interaction and it was suggested that it may play an important role in the regulation of circulating levels of these lymphokines (Hession, Catherine et al. (1987) Science 237:1479–1484). Although uromodulin does not inhibit the cytotoxic activity of TNF-α as monitored by lysis of tumor cell targets, it interacts with recombinant TNF-α via carbohydrate chains and this interaction may be critical in promoting clearance and/or reducing in vivo toxicity of TNF and other lympyhokines (Sherblom, Anne P. (1988) J. Biol. Chem. 263:5418–5424). In a recent publication by Seckinger et al. (J. Exp. Med. (1988) 167:1511–1516) a human inhibitor of TNF-α obtained from the urine of febrile patients was described as a 40–60 Kda protein inhibiting the cytotoxic activity of TNF-α. It was shown to differ from uromodulin and from the above-mentioned IL-1 inhibitor.

SUMMARY OF THE INVENTION

The present invention provides substantially purified TNF Inhibitory Protein which can antagonize the effects of TNF. This antagonism can be determined both by measuring reduction of the cytotoxic activity of TNF as well as by measuring interference with TNF binding to its receptors.

The invention is directed to said TNF Inhibitory Protein in substantially purified form, as well as to its salts, functional derivatives and active fractions thereof.

The invention also relates to a process for the purification of TNF Inhibitory Protein.

The invention further concerns recombinant DNA molecules comprising the nucleotide sequence coding for said protein, expression vehicles comprising them and host cells transformed therewith.

The substantially purified TNF Inhibitory Protein of the invention is used as the active ingredient of pharmaceutical compositions and in medical treatments to protect mammals against the deleterious effects of TNF.

DESCRIPTION OF THE FIGURES

FIG. 5 shows the separation of TNF Inhibitory Protein on reversed phase HPLC. The active protein eluted from Mono Q 5/5 was injected in one 1.6 ml portion on an Aquapore RP-300 HPLC column (Brownlee Labs) run with 0.3% aqueous TFA (buffer F) in water at a flow rate of 0.5 ml/minute. The column was then eluted with a linear gradient of acetonitrile in buffer F from 0 to 20% for 5 minutes, followed by a linear gradient from 20–50% for 60 minutes and then with a linear gradient from 50–80% for 5 minutes (----). Fractions of 0.5 ml were collected and tested for inhibition of TNF cytotoxicity on murine A9 cells. The protein concentration was monitored during elution by measuring relative fluorescence of representative samples of each fraction, after automated reaction with fluorescamine (—). The TNF inhibitory activity eluted as a sharp peak together with an Isolated peak of protein.

DETAILED DESCRIPTION OF THE INVENTION

The present invention provides substantially purified TNF Inhibitory Protein and salts, functional derivatives and active fractions thereof, having the ability to inhibit the binding of TNF to its receptors and the cytotoxic effect of TNF.

It was found according to the present invention that the TNF Inhibitory Protein is able to inhibit the biological activities of both TNF-α and TNF-β and thus the inhibition of these two cytokines, herein referred to as TNF, by the TNF Inhibitory Protein, is encompassed by the present invention.

The TNF Inhibitory Protein of the invention may be found in human urine. When crude preparations thereof derived from human urine concentrate were chromatographed on Ultrogel ACA 44 gel filtration column, it showed an apparent molecular weight of 40–80 kDa. The substantially purified protein, which is substantially free of proteinaceous impurities, has a molecular weight of about 26–28 Kda when analysed by SDS.PAGE under reducing conditions and it moves as a single peak on reversed-phase high performance liquid chromatography (HPLC). Its activity is determined by its ability to inhibit the binding of TNF-α to its cell surface receptors on human HeLa and FS11 fibroblast cells and/or by its ability to inhibit the cytotoxic effect of TNF-α on murine A9 cells.

It is further characterized by containing at the N-terminus the following amino-acid sequence:

```
       1               5              10              15
Asp-Ser-Val-Cys-Pro-Gln-Gly-Lys-Tyr-Ile-His-Pro-Gln-X-Asn-Ser
``` wherein the amino acid designed X at the 14th position was not identified and the presence of cysteine (Cys) at the 4th position is theoretical, since PTH (Phenyl thiohydantoin) Cys cannot be identified as such and no other residue was detected in this position.

As used herein the term 'salts' refers to both salts of carboxyl groups and to acid addition salts of amino groups of the protein molecule. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

"Functional derivatives" as used herein covers derivatives which may be prepared from the functional groups which occur as side chains on the residues or the N- or C-terminal groups, by means known in the art, and are included in the invention as long as they remain pharmaceutically acceptable, i.e. they do not destroy the activity of the protein and do not confer toxic properties on compositions containing it.

These derivatives may, for example, include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl group (for example that of seryl or threonyl residues) formed with acyl moieties.

As "active fractions" of the substantially purified protein, the present invention covers any fragment or precursors of the polypeptide chain of the protein molecule alone or together with associated molecules or residues linked thereto, e.g. sugar or phosphate residues, or aggregates of the protein molecule or the sugar residues by themselves, provided said fraction has the ability to inhibit the binding of TNF to its receptor and to inhibit the cytotoxic effect of TNF on cells.

Figure 1A:
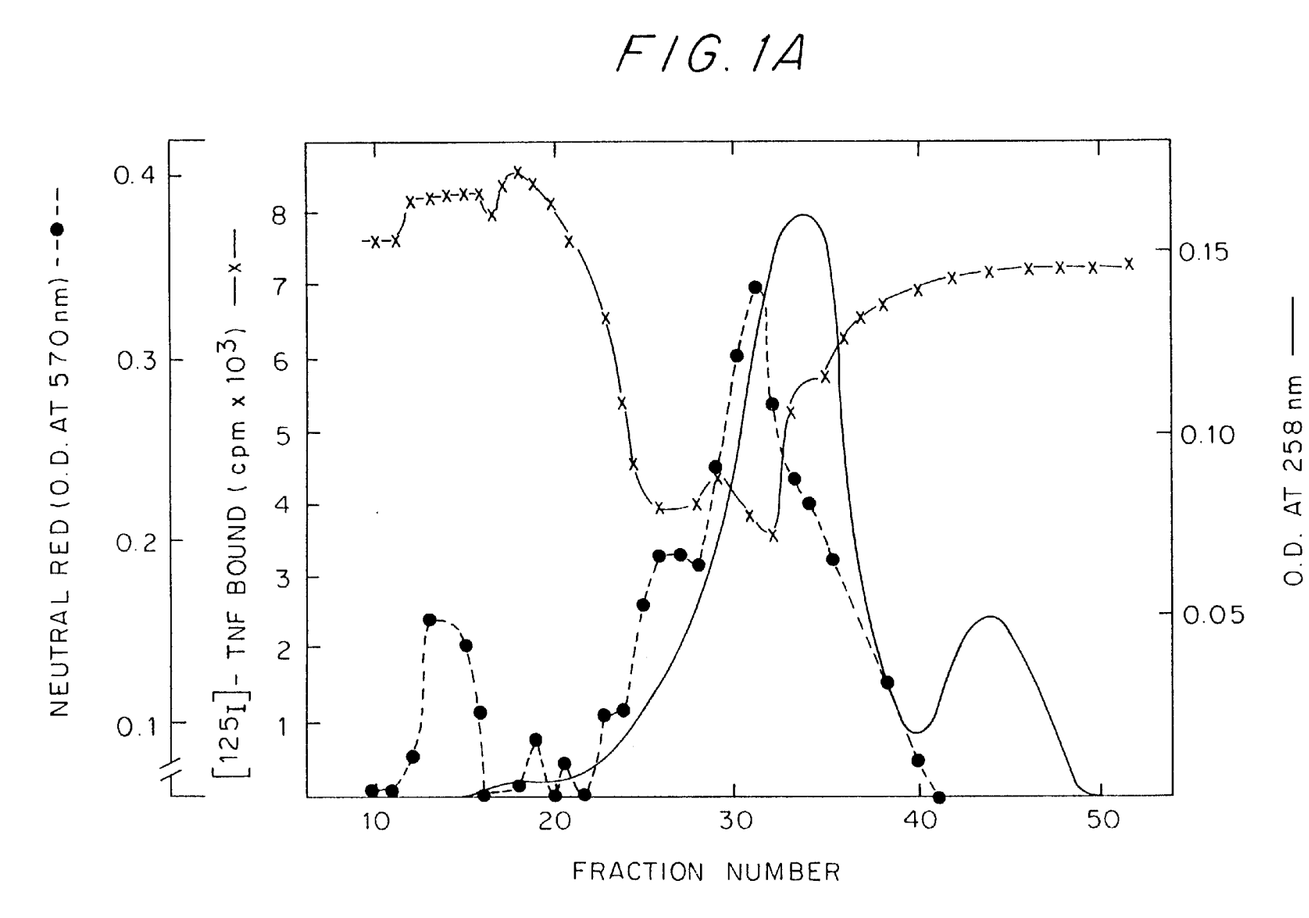
FIG. 1A shows the elution pattern of the TNF Inhibitory Protein from an Ultrogel ACA 44 gel filtration column. Two (2) ml fractions were collected and tested for protein content by absorption at 256 nm (—), for interference with $^{125}$I-TNFα binding to its cell surface receptor (x—x) and for inhibition of TNF-α cytotoxic activity (●—●). The major peak of TNF inhibitory activity eluted slightly before the majority of the protein.
Figure 1B:
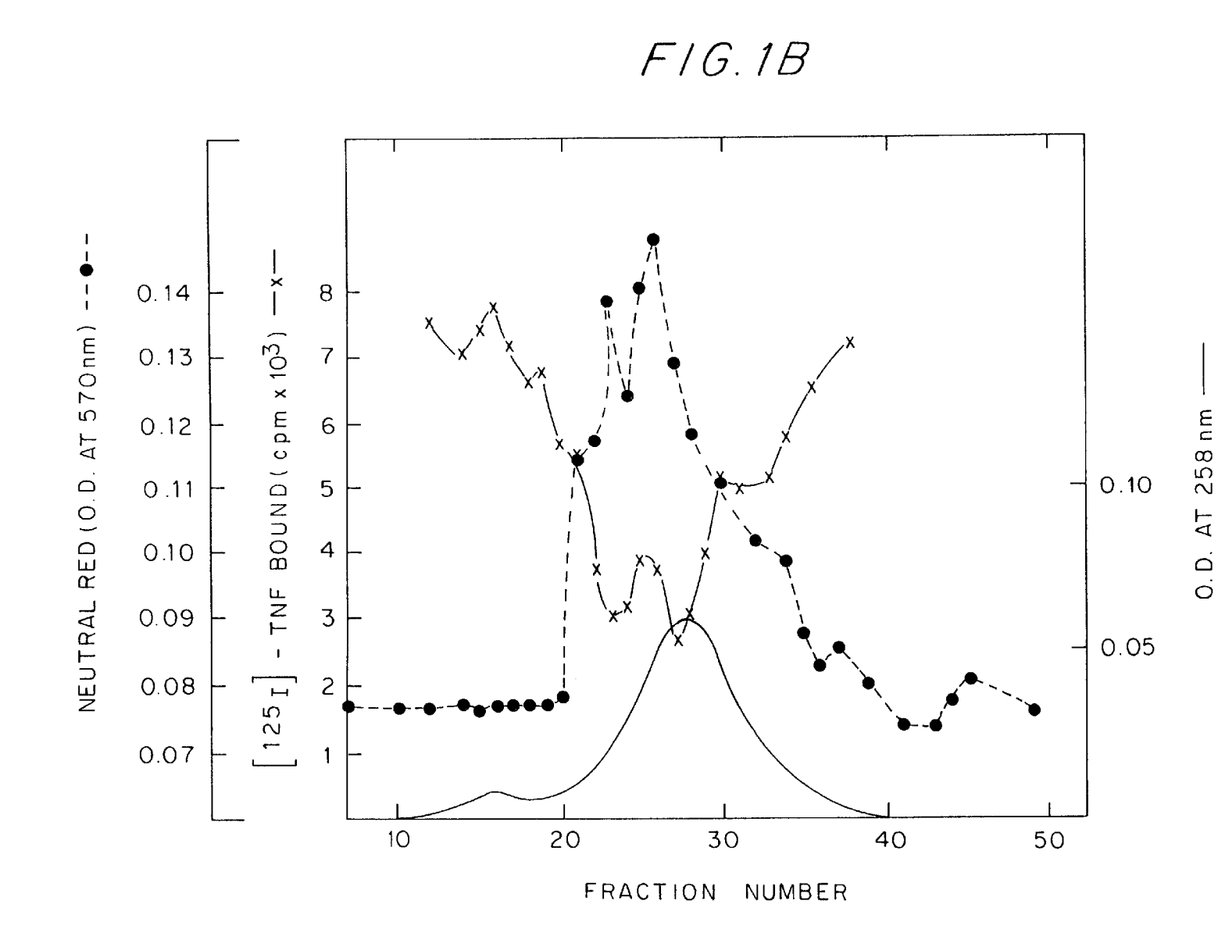
FIG. 1B shows the elution pattern of the TNF Inhibitory Protein when dialyzed against water prior to application on the Ultrogel ACA 44 gel filtration column. Two ml fractions were collected and assayed an in FIG. 1A. The dialysis against water did not change the elution pattern when compared with FIG. 1A.

1. Preliminary Characterization and Initial Purification of the TNF Inhibitory Protein In a preliminary characterization in the crude state, the following properties and activities of the protein were observed:

a) The TNF inhibitory activity could be found in the urine of healthy as well as of sick donors;

b) The active protein was not dialyzable through membranes with a molecular weight cut off of 10 kDa;

c) The apparent molecular weight of the active TNF Inhibitory Protein, when chromatographed on an Ultrogel ACA 44 gel filtration column, was found to be between 40 and 80 kDa. Extensive dialysis against water did not change the behaviour of the protein in this procedure (FIGS. 1A and 1B);

d) The isoelectric point of the active protein as determined by preparative isolectric focusing was between pH 6 and 8;

e) The active protein bound in part to Concanavalin-A Sepharose and could be specifically eluted with methyl-α-D-mannopyranoside which suggests that the protein is glycosylated;

f) The TNF inhibitory activity was heat labile;

g) A variety of protease inhibitors did not interfere with the biological activity of the TNF Inhibitory Protein indicating that the mechanism underlying the TNF inhibition could not be explained by proteolytic activities present in crude urine; and h) Inhibition of the binding of TNF-α to its cell surface receptors occurred only when the crude protein mixture containing the TNF Inhibitory Protein was applied simultaneously with TNF (Table 1).

The TNF Inhibitory Protein of the present invention differs thus from uromodulin by several of the above characteristics, such as by (a) its apparent molecular weight in gel filtration, (b) its isoelectric point, and (c) the fact that no extensive aggregation of the protein could be observed when dialyzed against water.

Partially purified TNF Inhibitory Protein preparations were obtained by fractionation of the urinary proteins by gel filtration, according to the following procedure:

Urine was concentrated by ultrafiltration with a membrane of a molecular weight cut-off of 10 kDa and then further by ultrafiltration with a membrane of a molecular weight cut-off of 5000 (Amicon YM5 membrane). The concentrate was dialyzed against PBS (Phosphate buttered saline) containing 1 mM $Mg^{2+}$, 1 mM $Ca^{2+}$ and then loaded on a Concanavalin-A Sepharose column equilibrated with the same buffer. The column was washed and the proteins which had specifically bound to the column were eluted with 0.5M methyl-α-D-mannopyranoside. Most, but not all, of the activity Interfering with TNF-α binding to its receptor was found to specifically adsorb to the lectin and could be eluted with methyl-α-D-mannopyranoside.

A sample of 3.5 mg of the Concanavalin-A eluted proteins was dialysed against PBS and fractionated by gel filtration chromatography on a 2×45 cm Ultrogel ACA 44 column (LKB, Sweden). Absorption of the eluted proteins, at 258 nm, was determined (—) Fractions of 2 ml were collected and examined at a dilution of 1:20 for their ability to protect against TNF-α by following assay procedures 2.1 (x—x) and 2.2 described hereinafter, said last assay being modified so that TNF-α was applied at a concentration of 75 U/ml and Balb/c-CL.7 cells were used in the assay. Viability of the cells was examined 12 hours later by determining the uptake of neutral red dye) (●—●) (FIG. 1A).

An identical sample of the proteins eluting from Concanavalin-A was subjected to 48 hours dialysis against distilled water and then spun to remove insoluble proteins. It was lyophylized and then reconstituted in PBS and subjected to chromatography on the Ultrogel ACA 44 column as above. Fractions were collected and assayed as above. There is no significant change in the fractionation pattern of the protective activity (FIG. 1B). When compared with the retention time of molecular markers (bovine serum albumin 67 kDa, ovalbumin 43 kDa, soybean trypsin inhibitor 20.1 kDa and cytochrome C 12.3 kDa), the activity was found to elute somewhat prior to the major protein peak with maximal activity at an apparent molecular weight of about 50 to 70 KDa.

TABLE I

EXAMINATION OF THE EFFECT OF THE TNF INHIBITORY PROTEIN-CONTAINING URINE CONCENTRATE BY APPLYING IT ON CELLS PRIOR TO, OR TOGETHER WITH TNF-α
Binding of $^{125}$I-TNF-α a to cells, Effect of the TNF Inhibitory Protein when applied:

| Urine donor | A At 4° C. 90' prior to application of TNF-α | | B At 37° C. 90' prior to application of TNF-α | | C At 4° C. together with TNF-α | |
|---|---|---|---|---|---|---|
| | CPM | % Binding | CPM | % Binding | CPM | % Binding |
| none | 5290 | 100% | 5560 | 100% | 4630 | 100% |
| 1 | 4600 | 87% | 4460 | 80% | 880 | 19% |
| 2 | 5260 | 99% | 4730 | 85% | 2450 | 53% |
| 3 | 5160 | 98% | 4730 | 85% | 910 | 20% |
| 4 | 4560 | 86% | 4730 | 85% | 1340 | 29% |

Decrease of $^{125}$I-TNF-α binding to the cells by the TNF Inhibitory Protein present in the urine concentrate is observed only when $^{125}$I-TNF-α and the protein are applied together on calls and not when the protein is first applied on calls and then removed prior to the application of TNF-α. This indicates that the interference with TNF-α binding to cells is not due to an effect of the TNF Inhibitory Protein on the cells, nor is it due to presence of TNF-α itself in the urine, but It rather reflects some kind of interaction between the protein of the invention and TNF-α.

2. Assays for the TNF Inhibitory Protein of the Invention

Two assay procedures were used for monitoring the activity of the TNF Inhibitory Protein in the different fractions during the purification process.

2.1 Inhibition of Binding of TNF-α to its Receptor

The assay procedure for the quantitation of TNF binding to cells was performed as described (Israel, S. et al. (1986) Immunol. Letters 12:217–224; Holtmann, H. and Wallach, B. (1987) J. Immunol. 139: 1161–1167).

Cells (HeLa or FS11) foreskin fibroblast cells) were seeded in DMEM (Dulbecco's Modified Eagle's Minimal Essential Medium) at a density of $2.5 \times 10^3$ cells/well in 15 mm well plates. After a 24-hour incubation at 37° C. in 5% $CO_2$, the plates were transferred to ice, the growth medium was removed and aliquots of the samples containing the TNF Inhibitory Protein were mixed with 10 units of labelled $^{125}$I-TNF-α ($10^5$ cpm) in 0.15 ml phosphate buttered saline (PBS) supplemented with 1 mM $Ca^{2+}$ and 1 mM $Mg^{2+}$, 0.5 mg/ml bovine serum albumin (BSA) and 0.1% sodium azide (PBS/BSA) and were applied to the cells and incubated for 2 hours at 4° C. Cells were then rinsed with PBS/BSA, transferred to vials for radioactivity measurement and their associated label was quantitated in a gamma counter. Unspecific binding was determined by adding excess of unlabeled TNF to the assay and the value was substracted in all the cases.

2.2 Inhibition of the Cytotoxic Activity of TNF-α

This bioassay was developed based on the cytotoxic effect of TNF on cycloheximide (CHI)-sensitized cells and its quantitation by the neutral-red uptake method, as described in Wallach, D. (1984) J. Immunol. 132:2464–2469.

Samples to be tested for the presence of the protein were diluted two-fold serially, at 4° C., in DMEM and an equal volume of the same medium containing 40 Ug/ml TNF-α and 400 μg/ml oycloheximide (CHI) is added thereto.

Murine A9 cells were seeded in 96-well flat-bottom microtiter plates ($1.5 \times 10^4$ cells/well) with 100 μl DMEM-CS (DMEM containing 5% fetal calf serum and 5% calf serum).

100 μl aliquots of the serially diluted protein TNF-α-CHI mixtures were applied to each well and the cells were further incubated for 14 hours.

Viability of the cells was determined by incubation with neutral red for 2 hours, washing away excess dye, extracting the neutral red that was taken up by the cells with Sorenson's citrate buffer-ethanol mixture, and quantitating it chronometrically at 570 nm with a Microelisa Auto-reader.

1 U/Ml of TNF inhibitor activity was defined as the dilution factor giving a statistically significant protection from TNF killing ($p<0.05$).

The bioassay is preferably used in the present invention for monitoring the activity of the protein during purification because it is less laborious and does not involve the use of radiolabelled material. There is no need to transfer the cells from individual wells to counting vials and multiple assays can be scored rather rapidly with the use of the Microelisa Auto-reader.

Figure 2A:
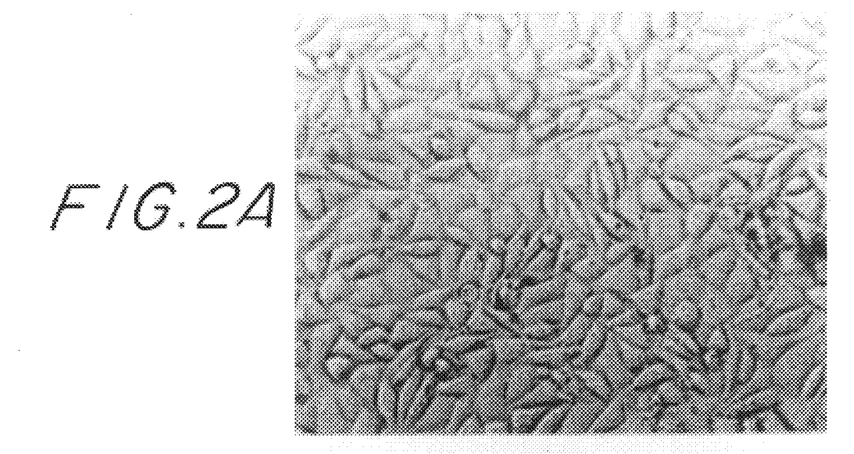
FIGS. 2A–2C show the morphology of murine A9 cells treated with cycloheximide (CHI) (FIG. 2A), with TNF-α-CHI (FIG. 2B) and with THF-α-CHI together with the TNF Inhibitory Protein (FIG. 2C).
Figure 2B:
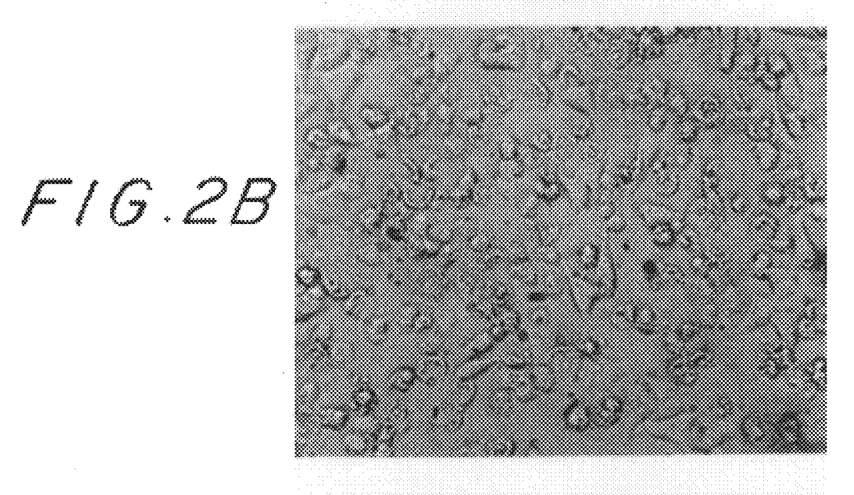
Figure 2C:
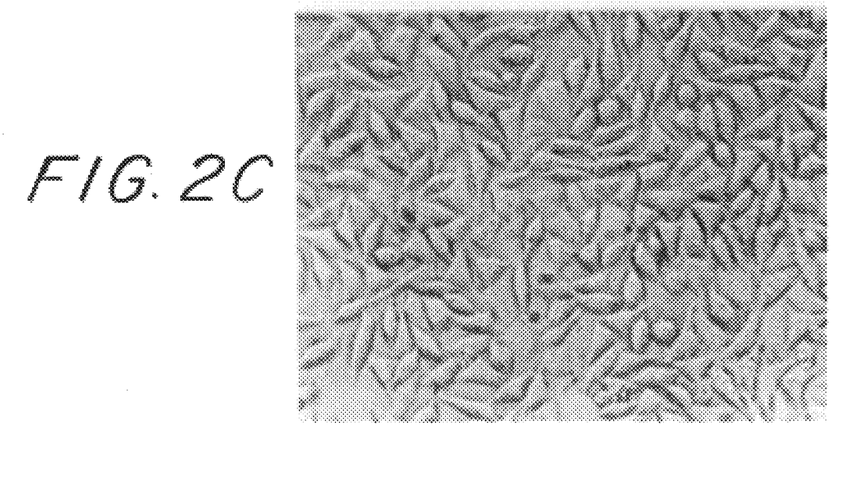

The morphology of murine A9 cells treated under conditions according to this bioassay is shown in FIGS. 2A–2C. In FIG. 2A are shown cells incubated with CHI only, in FIG. 2B are cells incubated with a TNF-α-CHI mixture and in FIG. 2C are cells incubated with a TNF-α-CHI mixture together with a sample of the TNF Inhibitory Protein (following CM-Sepharose purification, as described hereinafter). The protective effect of the TNF Inhibitory Protein against the cytotoxic effect of TNF-α is very clear in FIG. 2C.

3. Purification of the TNF Inhibitory Protein

In the preferred embodiment of the invention, the substantially purified protein of the invention is produced by a process which comprises:

a) recovering the crude protein fraction from a dyalized concentrate of human urine;

b) subjecting said crude protein fraction of step (a) to ion exchange chromatography to obtain partially purified active fractions of the TNF Inhibitory Protein defined by its ability to inhibit both the binding of TNF to its receptors and the cytotoxic effect of TNF;

c) applying said partially purified active fractions of the TNF Inhibitory Protein from step (b) to reversed phase high pressure liquid chromatography (HPLC) to obtain substantially purified active fractions of the TNF Inhibitory Protein defined by its ability to inhibit both the binding of TNF to its receptors and the cytotoxic effect of TNF; and d) recovering the substantially purified protein of step (c), said protein having a molecular weight of about 26–28 kDa on SDS PAGE under reducing conditions, moving as a single peak on reversed phase HPLC and having the ability to inhibit both the binding of TNF to its receptors and the cytotoxic effect of TNF.

The ion exchange chromatography of step (b) is preferably performed in 3 steps and includes chromatographic purification in Carboxymethyl Sepharose, Mono S HR 5/5 FPLC and Mono Q HR 5/5 FPLC columns, preferably in this sequence. The reversed phase HPLC is preferably performed in an Aquapore RP300 column.

In a preferred embodiment, in all steps of the purification, the procedure was monitored by measuring the protein concentration (absorbance at 280 nm or relative fluorescence following automatic reaction of representative aliquots with fluorescamine) and the inhibition of the TNF-α cytotoxic activity according,to the bioassay described in 2.2 above.

3.1 Preparation of the Urine Concentrate

A pool of 200 l male urine from healthy donors was subjected to micro filtration on a Pellicon membrane with a pore size of 0.45 μm. The filtrate was concentrated by ultrafiltration using a Pellicon membrane with a molecular weight cut off of 10 kDa to a final volume of 500 ml. The concentrate was dialyzed against phosphate buffered saline containing 1 mM benzamidine and 0.1% sodium azide.

3.2 Carboxy Methyl (CM) Sepharose Chromatograpby

A $2.7 \times 10$ cm CM-Sepharose cation exchange column (Pharmacia) was prewashed with 1 M NaCl, 10 mM citric acid buffer, pH 5.0, containing 0.02% sodium azide (buffer C) and equilibrated with 10 mM citric acid buffer, pH 5.0, containing 0.02% sodium aside (buffer A). The urine concentrate of step 3.1 above was dialysed against 2 changes of 100× sample volume buffer A and spun for 15 minutes at 8000 rpm. The supernatant was applied at 4° C. on the CM-sepharose column at a flow rate of 2 ml/minute and fractions of 50 ml were collected. The column was washed with buffer A until no protein could be detected (about 1500 ml) and then eluted with 5× col. volumes of 200 mM NaCl, 10 mM citric acid buffer, pH 5.0, containing 0.02% sodium azide (buffer B) (5 fractions) followed by elution with 3× col. volumes of buffer c (3 fractions). The fractions were collected and tested as indicated. The major portion of the biological activity of the TNF inhibitory protein was found in the second fraction of the elution with buffer B.

3.3 Cation-Exchange Mono S HR 5/5 FPLC Chromatography

Figure 3:
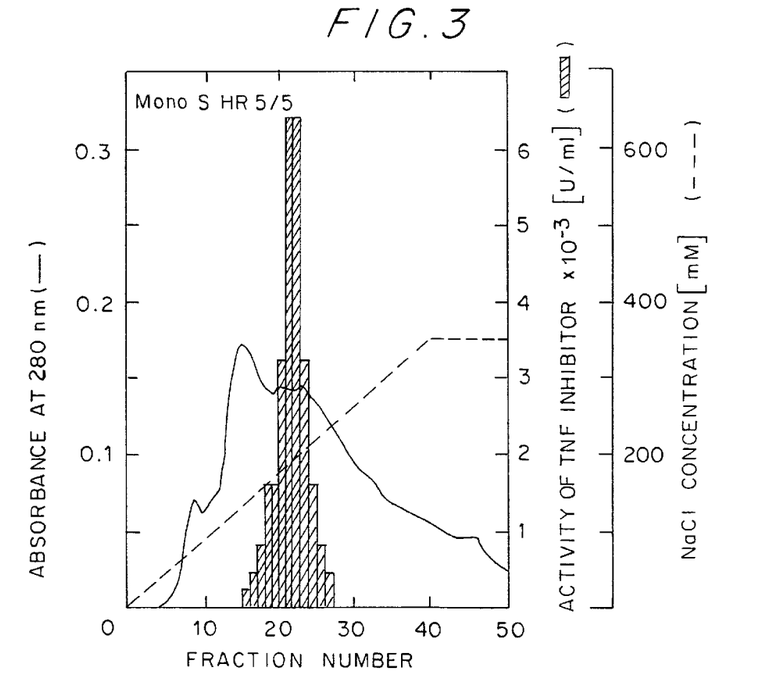
FIG. 3 shows the results of the second step of the purification of the TNF Inhibitory Protein. Carboxy methyl (CM) Sepharose purified TNF Inhibitory Protein was loaded in 8×2 ml portions on a Mono S 5/5 cation exchange column and eluted with a linear gradient from 0 to 350 mM NaCl (----) in a buffer containing 10 mM citric acid, 0.02% sodium aide, pH 5.0. At a flow rate of 0.5 ml/minute, fractions of 0.5 ml were collected and assayed for inhibition of TNF cytotoxicity on murine A9 cells. The majority of the TNF Inhibitory Protein eluted at a salt concentration of 180 to 200 mM NaCl (▨). The protein was monitored by absorption at 280 nm (—).

The Mono SHR 5/5 column (Pharmacia) was prewashed with a 10 mM citric acid buffer, pH 5.0. containing 0.02% sodium azide (buffer A) until a stable baseline was demonstrated (monitored at 280 nm by a UV detector). The active fractions eluted from the CM-Sepharose column were pooled and dialysed against 2 changes of 100× sample volume buffer A. The sample was injected in 8×2 ml portions onto the column until the maximum binding capacity of the column was reached (28 mg). The column was washed with buffer A until a flat baseline was seen. The bound proteins were eluted with a linear NaCl gradient (0–350 mM) in buffer A. The gradient was run for 40 minutes at a flow rate of 0.5 ml/minute. Then the column was washed for 10 minutes with 350 mM NaCl in Buffer A (Buffer D). The proteins which could not be eluted in a concentration of 350 mM NaCl were then eluted from the column with Buffer C. Fractions of 0.5 ml were collected and assayed as indicated. The results are shown in FIG. 3. The major portion of the activity was found to elute in fractions 20–23, corresponding to 100–220 mM NaCl.

3.4 Anion-exchange Mono Q HR 5/5 FPLC Chromatography

Figure 4:
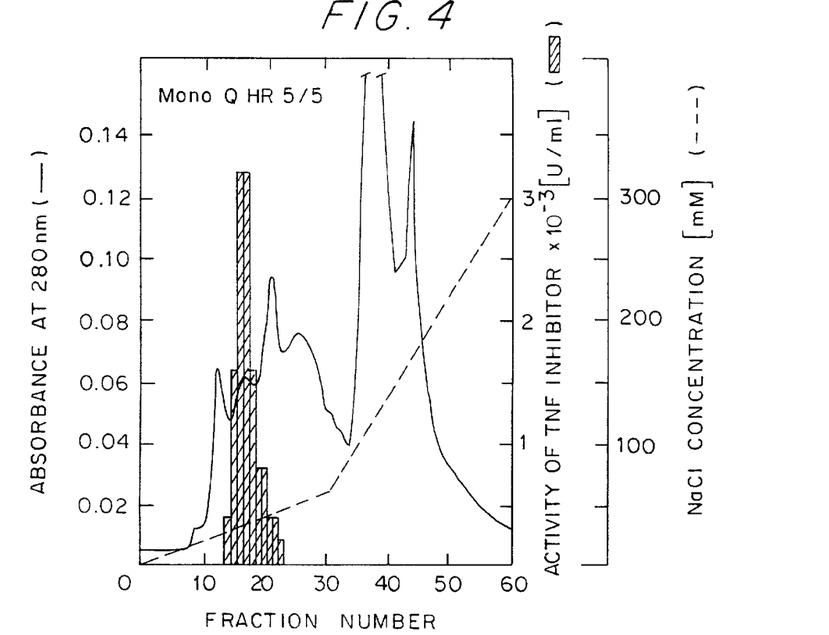
FIG. 4 shows the results of the third step of the purification of the TNF Inhibitory Protein. The active protein obtained by purification on CM-Sepharose and Mono S was dialyzed against a buffer containing 5 mM sodium borate, 0.02% sodium azide, pH 9.0 and loaded on a Mono Q 5/5 anion exchange column. The bound proteins were eluted at a flow rate of 0.5 ml/minute with a linear salt gradient from 0 to 60 mM NaCl and then from 60 to 300 mM NaCl (----). Fractions of 0.5 ml were collected and tested for inhibition of TNF cytotoxicity on murine A9 cells (▨). The protein was monitored during elution by measuring the absorption at 280 nm (—). As shown, most of the activity eluted at a salt concentration of 30 to 40 mM.
Figure 5:
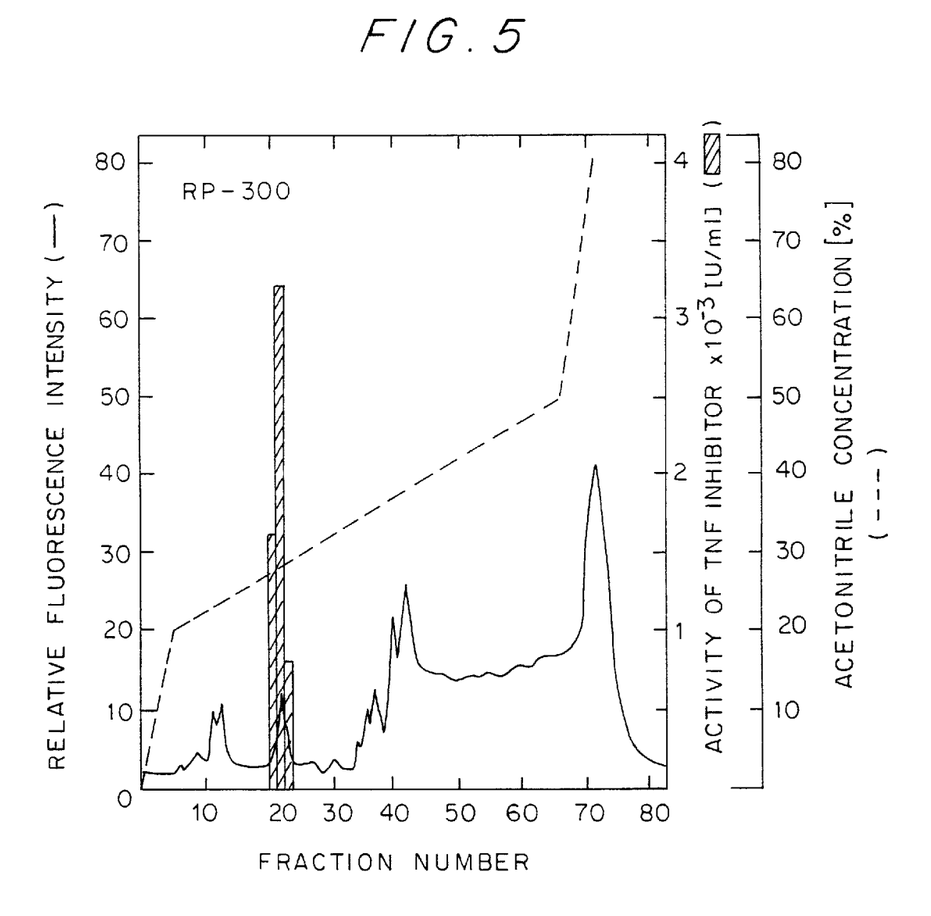

The Mono Q HR 5/5 column (Pharmacia) was prewashed with a 5 mM sodium borate buffer, pH 9.0, containing 0.02% sodium azide (buffer E) until a stable baseline was achieved. The active fractions eluted from the Mono S column were pooled and dialyzed against 2 changes of 100× sample volume buffer E. The sample was injected in 2 ml portions onto the column and the column was run with buffer E until the baseline was flat. The bound proteins were eluted by a 30 mM linear NaCl gradient of 0–60 mM in buffer E, followed by a 30 minute linear gradient from 60 to 300 mM NaCl in buffer E. The column was then washed for 10 minutes with 300 mM HaCl in Buffer E and for 4 minutes with a 1 M NaCl in Buffer E at a flow rate of 0.5 ml/minute. Fractions of 0.5 ml were collected and tested for activity and for protein content. As shown in FIG. 4, the majority of the activity eluted in fractions 15–18 at a NaCl concentration of approximately 40 mM.

3.5 Reversed-phase High Pressure Liquid Chromatography (HPLC)

The reversed-phase HPLC column Aquapore RP 300 4.6×30 mm (Brownlee Labs) was prewashed with 0.3% aqueous trifluoroacetic acid (TFA) (Buffer F) until a stable baseline was obtained by the fluorescamine detection system. The active fractions which were eluted from the Mono Q column were pooled and injected in one 1.6 ml portion onto the column. The column was run with Buffer F at a flow rate of 0.5 ml/minute until the fluorometer did not detect any protein. The column was then eluted at a flow rate of 0.5 ml/minute, with a 0–20% linear gradient of acetonitrile in Buffer F for 5 minutes, followed by a 20–50% linear gradient of acetonitrile for 60 minutes and finally a 50% to 80% linear acetonitrile gradient for 5 minutes. The column was then washed for 15 minutes with 80% acetonitrile. Fractions of 0.5 ml were collected and eluted for protein content and for activity. As shown in FIG. 4, the activity sharply eluted in fractions 21–23 (peaking in fraction 22) together with an isolated protein peak. These fractions corresponded to 27% acetonitrile.

3.6 SDS-PAGE

In order to monitor the result of the purification, sodium dodecyl sulphate polyacrylamide gel electrophoresis (SDS-PAGE) was performed according to the method of Laemmli U. K., et al. (1970) Nature 227:690. A sample of the active fractions eluting from the ion exchange columns of steps 3.2, 3.3 and 3.4 containing 5 μg of protein or a sample of 40 μl of the fractions 21–23 derived from the reversed phase HPLC, were mixed with 3×concentrated sample buffer containing 6% SDS (w/v) and 15% v/v β-mercaptoethanol and loaded on a 15% acrylamide gel. As a reference for molecular weight, a mixture of molecular weight markers (α lactalbumin 14.4 kDa, soya bean trypsin inhibitor 20.1 kDa, carbonic anhydrase 30 kDa, ovalbumin 43 kDa, bovine serum albumin 67 kDa, and phosphorylase b. 94 kDa) was treated as above and loaded. A blank with sample buffer was also run. The gel was run at 160 volt and the protein bands were visualized by silver staining (Oakley, B. R. et al. Anal. Biochem. 105:361). The purified TNF Inhibitory Protein moved as a single band with an apparent molecular weight of 26–28 kDa (not shown).

3.7 Automated Protein Micro-sequence Analysis

Samples of the substantially purified TNF Inhibitory Protein of the invention (1–5 μg, 50–200 pmol each) were applied to pretreated, biobrene-coated glass-fiber disc. The dried discs were subjected to repetitive cycles of Edman degradation in an automated pulsed liquid-gas-phase protein microsequencer (Model 475) with an on-line HPLC PTH-amino acid analyzer (Model 120) and a data acquisition and processing unit Model 900, all from Applied Biosystems Inc. Foster City, Calif., U.S.A.). The computer-derived sequence was compared with the raw data and was corrected when necessary. Altogether three separate analyses were performed in order to confirm the sequence date. The initial yield was over 40%, indicating that the major protein in the preparation (the 27 kDa band) is related to the resulting sequence.

The N-terminal sequencing of the TNF Inhibitory Protein gave the following amino acid sequence.

```
         1               5              10              15
Asp-Ser-Val-Cys-Pro-Gln-Gly-Lys-Tyr-Ile-His-Pro-Gln-X-Asn-Ser
```

The amino acid at the 14th position was not identified. As to the cysteine residue at the 4th position, its presence is theoretical since PTH (Phenyl thiohydantoin) cys cannot be identified as such and no other amino acid residue was detected in this position.

A computerized search in the National Biomedical Research Foundation protein library (update No. 16) by the FASTP method did not reveal a significant homology to any known protein.

4. Genetic Engineering of the TNF Inhibitory Protein

This invention further concerns DNA molecules comprising the nucleotide sequence coding for the TNF Inhibitory Protein of the invention, replicable expression vehicles containing said DNA molecules, hosts transformed therewith and the TNF Inhibitory Protein produced by expression of such transformed hosts. The term "DNA molecules" includes genomic DNA, cDNA, synthetic DNA and combinations thereof.

The cloning of the TNF Inhibitory Protein may be carried out by different techniques. According to one approach, specific antibodies (polyclonal or monoclonal) to the TNF Inhibitory Protein are produced and used to clone the TNF Inhibitory Protein cDNA. This approach is comprised of the following three steps:

a) Preparation of Antibodies

The antibodies to the TNF Inhibitory Protein can be produced either by using the substantially purified TNF Inhibitory Protein of the present invention or by using one or more synthetic peptides identical to the known sequence of the protein, e.g. the N-terminal protein sequence, or by fusing one of the possible nucleotide sequences deduced from the amino acid sequence of the TNF Inhibitory Protein to the gene coding for Protein A and expressing the fused Protein A—TNF Inhibitory Protein in E. coli.

For obtaining polyclonal antibodies, the substantially purified TNF Inhibitory Protein or the synthetic peptides linked to a carrier protein are injected into rabbits. For the production of monoclonal antibodies, the fused Protein A—TNF Inhibitory Protein synthetic gene is expressed in *E. coli*, the fused protein obtained is purified by affinity chromatography on IgG Sepharose column and injected into mice. Alternatively, the substantially purified TNF Inhibitory Protein of the present invention is injected into mice.

b) Screening of TNF Inhibitory Protein Producing Cells

The antibodies to TNF Inhibitory Protein are used to search for cells producing the TNF Inhibitory Protein by immunofluorescence or by Western blot.

c) Preparation of cDNA from Producing Cells mRNA is extracted from TNF Inhibitory Protein producing cells and cDNA is prepared by the use of reverse transcriptase. The cDNA is cloned in an expression vector such as λgT 11 and screened by the use of the antibodies.

fragments thereof and to characterize their amino acid sequence. In order to obtain peptide fragments, purified protein preparations are subjected to fragmentation, e.g. by digestion with proteases such as trypsin, chymotrypsin or papain by methods well known in the art (Oike, Y. et al. (1982) J. Biol. Chem. 257:9751–9758). The peptide fragments produced by digestion are separated by reverse phase HPLC and sequenced by automatic amino acid sequencing techniques.

An already described, the sequence corresponding to the first 16 amino acids at the N-terminal portion of the protein was determined by analysis of the substantially purified TNF Inhibitory Protein in an automatic sequencer and the following amino acid sequence was obtained:

```
     1               5                10                15
Asp-Ser-Val-Cys-Pro-Gln-Gly-Lys-Tyr-Ile-His-Pro-Gln-X-Asn-Ser
```

The λgt 11 expression vector can be used for insertion of DNA up to 7 kb in length at a unique EcoRI site 53 bases upstream from the β-galactosidase termination codon. Therefore, foreign sequences DNA may be inserted into this site and expressed under appropriate conditions as fusion proteins. The λgt 11 expression vector is particularly useful for the construction of cDNA libraries to be screened with antibody probes (Huynh, T. V. et al. in: David Glover (ed.), *DNA Cloning Techniques: A Practical Approach*, IRL Press, Oxford (1984) pp. 49–78), as outlined here.

Following another approach, a synthetic oligonucleotide or a mixture of synthetic oligonucleotides, whose sequence is derived from the sequence of a fragment of the protein, e.g., the N-terminal amino acid sequence of the TNF Inhibitory Protein are produced and this oligonucleotide or the mixture of oligonucleotides are used as a probe for cloning the cDNA or the genomic DNA coding for the TNF Inhibitory Protein.

The genomic DNA may or may not include naturally occurring introns. It may be obtained, for example, by extraction from suitable cells and purification by means well known in the art. Suitable DNA preparations, such as human genomic DNA, are enzymatically cleaved by restriction enzymes, or randomly sheared, and the fragments inserted into appropriate recombinant vectors to form a gene library. Such vectors can then be screened with synthetic oligonucleotide probes in order to identify a sequence coding for the TNF Inhibitory Protein of the invention.

Alternatively, mRNA is isolated from a cell which expresses the protein of the invention and used to produce cDNA by means well known in the art. This cDNA, after conversion to the double-stranded form, may be cloned and the resulting clone screened with an appropriate probe for cDNA coding for the desired sequences. Once the desired clone has been isolated, the cDNA may be manipulated in substantially the same manner as the genomic DNA. However, with cDNA there will be no introns or intervening sequences.

In order to synthesize the oligonucleotides to be used as probes, it is possible either to perform sequence analysis of the intact TNF Inhibitory Protein or to obtain peptide Once one or more suitable peptide fragments have been sequenced or a partial sequence of the protein is determined, the DNA sequences capable of encoding them are examined. Due to the degeneration of the genetic code, more than one codon may be used to encode a particular amino acid and one or more different oligonucleotides can be produced, each of which would be capable of encoding the TNF Inhibitory Protein peptide fragments (Watson, J. D., In: *Molecular Biology of the Gene*, 3rd ed., W. A. Benjamin, Inc. Menlo Park, Calif. (1977), pp. 356–357). However, only one member of the set contains the nucleotide sequence that is identical to the nucleotide sequence of the gene. Its presence within the set and its capability to hybridize to DNA even in the presence of the other members of the set, makes it possible to employ the unfractionated set of oligonucleotides in the same manner in which one would employ a single oligonucleotide to clone the gene that encodes the peptide. The use of such oligonucleotide or set of oligonucleotides containing the theoretical "most probable" sequence capable of encoding the TNF Inhibitory Protein gene fragments (following the "codon usage rules" disclosed by Lathe, R., et al. (1985) J. Molec. Biol., 183:1–12) permits to identify the sequence of a complementary oligonucleotide or set of oligonucleotides which is capable of hybridizing to the "most probable" sequence encoding the TNF Inhibitory Protein or at least a portion thereof, or a set of such sequences. This oligonucleotide containing such a complementary sequence may then be synthesized and employed as a probe to identify and isolate the gene of the TNF Inhibitory Protein of the invention (Maniatis, T. et al. *Molecular Cloning: A Laboratory Manual*, Cold spring Harbor Press, Cold Spring Harbor, N.Y. (1982).

Once a suitable oligonucleotide, or set of oligonucleotides, which is capable of encoding a fragment of the TNF Inhibitory Protein gene (or which is complementary to such an oligonucleotide, or set of oligonucleotides) is identified using the above-described procedure, it is synthesized and hybridized to a DNA or, preferably, to a cDNA preparation derived from cells which are capable of expressing the desired gene, preferably after the source of cDNA has been enriched for the desired sequences, e.g. by extracting DNA from cells which produce high levels of the desired gene and then converting it to the corresponding cDNA by employing the enzyme reverse transcriptase.

Procedures for hybridization of nucleic acids are common knowledge and are disclosed, for example, in Maniatis, T. *Molecular Cloning: A Laboratory Manual,* op. cit. and in Haymes, B. T., et al., *Nucleic Acid Hybridization: A Practical Approach,* IRL Press, Oxford, England (1985). By hybridization with the above nucleotide or set of oligonucleotides probes, it is possible to identify in a cDNA or genomic library, the DNA sequences capable of such hybridization and they are then analyzed to determine to what extent they contain encoding sequences for the TNF Inhibitory Protein of the invention.

By the same or similar techniques it has been possible to successfully clone the genes for several human proteins, such as the tissue-type plasminogen activator (Pennica, D. et al. (1983) Nature 301:214–221).

The DNA molecules coding for the TNF Inhibitory Protein of the invention, obtained by the above described methods, are then inserted into appropriately constructed expression vectors by techniques well known in the art (see Maniatis et al., op cit.). Double-stranded cDNA is linked to plasmid vectors by homopolymeric tailing or by restriction linking involving the use of synthetic DNA linkers or blunt-ended ligation techniques, DNA ligases are used to ligate the DNA molecules and undesirable joining is avoided by treatment with alkaline phosphatase.

In order to be capable of expressing a desired protein, an expression vector should comprise also specific nucleotide sequences containing transcriptional and translational regulatory information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example, the int promoter of bacteriophage $\lambda$, the bla promoter of the $\beta$-lactamase gene of pBR322, and the CAT promoter of the chloramphenicol acetyl transferase gene of pPR325, etc., or inducible, such as the prokaryotic promoters including the major right and left promoters of bacteriophage $\lambda$ ($P_L$ and $P_R$), the trp, recA, lacZ, lacI ompF and gal promoters of *E. coli,* or the trp-lac hybrid promoter, etc. (Glick, B. R. (1987) J. Ind. Microbiol. 1:277–282).

Besides the use of strong promoters to generate large quantities of mRNA, in order to achieve high levels of gene expression in prokaryotic cells, it is necessary to use also ribosome-binding sites to ensure that the mRNA efficiently translated. One example is the Shine-Dalgarno sequence (SD sequence) appropriately positioned from the initiation codon and complementary to the 3'-terminal sequence of 16S RNA.

For eukaryotic hosts, different transcriptional and translational regulatory sequences may be employed, depending on the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional Initiation regulatory signals may be selected which allow for repression and activation, so that expression of the genes can be modulated.

The DNA molecule comprising the nucleotide sequence coding for the TNF Inhibitory Protein of the invention and the operably linked transcriptional and translational regulatory signals is inserted into a vector which is capable of integrating the desired gene sequences into the host cell chromosome. The cells which have stably integrated the introduced DNA into their chromosomes can be selected by also introducing one or more markers which allow for selection of host cells which contain the expression vector. The marker may provide for prototrophy to an auxotropic host, biocide resistance, e.g., antibiotics, or heavy metals, such as copper, or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, M., (1983) Mol. Cel. Biol. 3:280.

In a preferred embodiment, the introduced DNA molecule will be incorporated into a plasmid or viral vector capable of autonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli,* for example, pBR322, ColE1, pSC101, pACYC 184, etc. (see Maniatis et al., *Molecular Cloning; A Laboratory Manual,* op.cit.); Bacillus plasmids such as pC194, pC221, pT127, etc. (Gryczan, T., *The Molecular Biology of the Bacilli,* Academic Press, New York (1982), pp. 307–329); Streptomyces plasmids including pIJ101 (Kendall, K. J. et al., (1987) J. Bacteriol. 169:4177–4183); Streptomyces bacteriophages such as $\theta$C31 (Chater, K. F. et al., in: *Sixth International Symposium on Actinomycetales Biology,* Akademiai Kaido, Budapest, Hungary (1986), pp. 45–54), and Pseudomona plasmids (John, J. F., et al. (1986) Rev. Infect. Dis. 8:693–704), and Izaki, K. (1978) Jpn. J. Bacteriol. 33:729–742).

Preferred eukaryotic plasmids include BPV, vaccinia, SV40, 2-micron circle, etc., or their derivatives. Such plasmids are well known in the art (Botstein, D., et al. (1982) Miami Wint. Symp. 19:265–274; Broach, J. R., in: *The Molecular Biology of the Yeast Saccharomyces: Life Cycle and Inheritance,* Cold Spring Harbor Laboratory, Cold Spring Harbor, N.Y., pp. 445–470 (1981); Broach, J. R. (1982) Cell 28:203–204; Bollon, D. P., et al. (1980) J. Clin. Hematol. Oncol. 10:39–48; Maniatis, T., In: *Cell Biology: A Comprehensive Treatise, Vol. 3: Gene Expression,* Academic Press, New York, pp. 563–600 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc.

Host cells to be used in this invention may be either prokaryotic or eukaryotic. Preferred prokaryotic hosts include bacteria such as *E. coli,* Bacillus, Streptomyces, Pseudomonas, Salmonella, Serratia, etc. The most preferred prokaryotic host to *E. coli.* Bacterial hosts of particular interest include *E. coli* K12 strain 294 (ATCC 31446), *E. coli* X1776 (ATCC 31537), *E. coli* W3110 (F$^-$, lambda$^-$, prototropic (ATCC 27325)), and other enterobacterium such as *Salmonella typhimurium* or *Serratia marcescens* and various Pseudomonas species. Under such conditions, the protein will not be glycosylated. The prokaryotic host must be compatible with the replicon and control sequences in the expression plasmid.

Preferred eukaryotic hosts are mammalian cells, e.g., human, monkey, mouse and chinese hamster ovary (CHO) cells, because they provide post-translational modifications to protein molecules including correct folding or glycosylation at correct sites. Also yeast cells can carry out post-translational peptide modifications including glycosylation. A number of recombinant DNA strategies exist which utilize strong promoter sequences and high copy number of plasmidse which can be utilized for production of the desired proteins in yeast. Yeast recognizes leader sequences on cloned mammalian gene products and secretes peptides bearing leader sequences (i.e., pre-peptides).

After the introduction of the vector, the host cells are grown in a selective medium, which selects for the growth of vector-containing cells. Expression of the cloned gene sequence(s) results in the production of the desired TNF Inhibitory Protein or a fragment thereof. The expressed protein is then Isolated and purified in accordance with the purification method described in the present application (section 3 supra) or by any other conventional procedure involving extraction, precipitation, chromatography, electrophoresis, or the like.

A further purification procedure that may be used in preference for purifying the protein of the invention is affinity chromatography. For this purpose, monoclonal antibodies to the TNF Inhibitory Protein are produced and immobilized on a gel matrix contained within a column. Impure preparations containing the recombinant protein are passed through the column. The protein will be bound to the column by the specific antibody while the impurities will pass through. After washing, the protein is eluted from the gel by a change in pH or ionic strength.

The monoclonal antibodies used in the present invention can be prepared using conventional hybridoma technique (Kohler et al. (1975) Nature 256:495; Kohler et al. (1976) Eur. J. Immunol. 6:511). In general, such procedures involve immunizing an animal with the desired purified protein antigen or with a synthetic peptide having the N-terminal sequence of the desired protein conjugated to a suitable carrier, such as bovine serum albumin. Spleen cells of such animals are isolated and fused with a suitable myeloma cell line. After fusion, the resulting hybridoma cells are selectively maintained in HAT medium and then cloned. The hybridoma cells obtained through such a selection are then assayed to identify clones which secrete antibodies capable of binding the TNF Inhibitory Protein. After identification, the desired clone can be grown in bulk, either in suspension culture or in ascitic fluid by injecting the cells into the peritoneum of suitable host mice.

The monoclonal antibodies produced by said hybridomas, after purification and immobilization, are very efficient for the purification of the TNF Inhibitory Protein in affinity purification procedure using an immuno-adsorbent column.

5. Utility and Compositions

The present invention further relates to pharmaceutical compositions comprising a pharmaceutically acceptable carrier and the substantially purified TNF Inhibitory Protein of the invention or its salts, functional derivatives or active fractions thereof, as active ingredient. These compositions may be used in any condition where there is an over production of endogenous TNF, such as in cases of septic shock, cachexia, graft-versus host reactions, autoimmune diseases like rheumatoid arthritis, etc. The way of administration can be via any of the accepted modes of administration for similar agents and will depend on the condition to be treated, e.g., intravenously in case of septic shock or local injection in case of rheumatoid arthritis, (for example, into the knee), or continuously by infusion, etc. The compositions may also be used in cases of TNF intoxication caused by exogenous administration of excessive amounts (overdoses) of TNF.

The pharmaceutical compositions of the invention are prepared for administration by mixing the protein or its derivatives with physiologically acceptable carriers, stabilizers and excipients, and prepared in dosage form, e.g. by lyophilization in dosage vials. The amount of active compound to be administered will depend on the route of administration, the disease to be treated and the condition of the patient. Local injection in case of inflammatory conditions of rheumatoid arthritis will require less TNF Inhibitory Protein on a body weight basis than will intravenous infusion in case of septic shock, etc.

The invention further relates to a method for treating conditions wherein TNF, either endogenously formed or exogenously administered, is to be eliminated from the body or its effect is to be antagonized, said method comprising administering to a patient in need of such a treatment, an amount of an agent selected from a substantially purified TNF Inhibitory Protein, a salt, a functional derivative or an active fraction thereof or a pharmaceutical composition comprising them, said amount being effective to antagonize the deleterious effect of TNF.

Various changes and modifications can be made in the present invention without departing from the spirit and scope thereof. The embodiments described herein are for the purpose of illustrating the invention without limiting the scope thereof.

We claim:

1. A protein capable of inhibiting the binding of TNF to cells and of inhibiting the cytotoxic effect of TNF, wherein said protein is obtainable from human urine and has the following features:

(a) it is a non-proteolytic protein capable of interacting with TNF so as to inhibit the binding of TNF to cell surface receptors and to inhibit the cytotoxic effect of TNF;

(b) the major peak of TNF inhibiting activity elutes slightly before the majority of the protein and shows an apparent molecular weight of about 40–80 kDa, when measured as a crude urine concentrate chromatographed on an Ultrogel AcA 44 filtration column; and (c) the isoelectric point of the active protein is between pH 6 and 8, when measured as a crude urine concentrate analyzed by electro-focusing.

2. A substantially purified protein obtainable from human urine, capable of interacting with TNF so as to inhibit the binding of TNF to cells and to inhibit the cytotoxic effect of TNF, said protein containing the following amino acid sequence:

Asp-Ser-Val-Cys-Pro-Gln-Gly-Lys-Tyr-Ile-His-Pro-Gln-X-Asn-Ser wherein X is an unidentified amino acid residue.

3. A pharmaceutical composition for use in treating conditions where TNF, either endogenously formed or exogenously administered, is to be eliminated from the body or its effect in the body is to be antagonized, comprising a protein in accordance with claim 2 and a pharmaceutically acceptable carrier.

* * * * *